US00PP27264P2

(12) United States Plant Patent
Oliver

(10) Patent No.: US PP27,264 P2
(45) Date of Patent: Oct. 11, 2016

(54) ***PHLOX* PLANT NAMED 'AURORA'**

(50) Latin Name: *Phlox×hybrida*
Varietal Denomination: Aurora

(71) Applicant: Charles G. Oliver, Scottdale, PA (US)

(72) Inventor: Charles G. Oliver, Scottdale, PA (US)

( * ) Notice: Subject to any disclaimer, the term of this patent is extended or adjusted under 35 U.S.C. 154(b) by 84 days.

(21) Appl. No.: 14/544,220

(22) Filed: Dec. 9, 2014

(51) Int. Cl.
*A01H 5/02* (2006.01)

(52) U.S. Cl.
USPC ..... Plt./320

(58) Field of Classification Search
USPC ..... Plt./320
See application file for complete search history.

*Primary Examiner* — Annette Para
(74) *Attorney, Agent, or Firm* — C. A. Whealy

(57) ABSTRACT

A new and distinct *Phlox* plant named 'Aurora', characterized by its upright and mounding plant form; vigorous growth habit; freely basal branching habit; early and freely flowering habit; large rounded inflorescences with white and pink-colored flowers; and resistance to Powdery Mildew.

2 Drawing Sheets

Botanical designation: *Phlox×hybrida.*
Cultivar denomination: 'AURORA'.

BACKGROUND OF THE INVENTION

The present invention relates to a new and distinct *Phlox* plant, botanically known as *Phlox×hybrida* and hereinafter referred to by the name 'Aurora'.

The new *Phlox* plant is a product of a planned breeding program conducted by the Inventor in Upper Tyrone Township, Pa. The objective of the breeding program is to create new vigorous *Phlox* plants with early flowering habit, attractive leaf and flower coloration and resistance to Powdery Mildew.

The new *Phlox* plant originated from an open-pollination in July, 2008 of an unnamed seedling selection of *Phlox maculata*, not patented, as the female, or seed, parent with an unknown selection of *Phlox×hybrida* as the male, or pollen, parent. The new *Phlox* plant was discovered and selected by the Inventor as a single flowering plant within the progeny of the stated open-pollination in a controlled environment in Upper Tyrone Township, Pa. in June, 2009.

Asexual reproduction of the new *Phlox* plant by vegetative stem cuttings in a controlled greenhouse environment in Upper Tyrone Township, Pa. since September, 2009 has shown that the unique features of this new *Phlox* plant are stable and reproduced true to type in successive generations.

SUMMARY OF THE INVENTION

Plants of the new *Phlox* plant have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Aurora'. These characteristics in combination distinguish 'Aurora' as a new and distinct *Phlox* plant:

1. Upright and mounding plant form.
2. Vigorous growth habit.
3. Freely basal branching habit.
4. Early and freely flowering habit.
5. Large rounded inflorescences with white and pink-colored flowers.
6. Resistance to Powdery Mildew.

Plants of the new *Phlox* differ from plants of the female parent selection in the following characteristics:

1. Plants of the new *Phlox* are shorter than plants of the female parent selection.
2. Inflorescences of plants of the new *Phlox* are rounded or dome-shaped whereas inflorescences of plants of the female parent selection are cylindrical in shape.
3. Plants of the new *Phlox* and the female parent selection differ in flower color as plants of the female parent selection have pink-colored flowers.

Plants of the new *Phlox* can be compared to plants of *Phlox carolina* 'Minnie Pearl', not patented. In side-by-side comparisons, plants of the new *Phlox* and 'Minnie Pearl' differed in the following characteristics:

1. Plants of the new *Phlox* were not as outwardly spreading and loose in plant habit as plants of 'Minnie Pearl'.
2. Plants of the new *Phlox* had shorter internodes than plants of 'Minnie Pearl'.
3. Leaves of plants of the new *Phlox* were glossier than leaves of plants of 'Minnie Pearl'.
4. Inflorescences of plants of the new *Phlox* faced upright whereas inflorescences of plants of 'Minnie Pearl' faced outwardly.
5. Inflorescences of plants of the new *Phlox* were rounded or dome-shaped whereas inflorescences of plants of 'Minnie Pearl' were flat-topped.
6. Inflorescences of plants of the new *Phlox* had more flowers per inflorescence than plants of 'Minnie Pearl'.
7. Plants of the new *Phlox* had slightly smaller flowers than plants of 'Minnie Pearl'.
8. Plants of the new *Phlox* and 'Minnie Pearl' differed in flower color as plants of 'Minnie Pearl' had white-colored flowers.

9. Plants of the new *Phlox* had shorter peduncles and pedicels than plants of 'Minnie Pearl'.

Plants of the new *Phlox* can also be compared to plants of *Phlox carolina* 'Kim' , not patented. In side-by-side comparisons, plants of the new *Phlox* and 'Kim' differed in the following characteristics:

1. Plants of the new *Phlox* were not as outwardly spreading as plants of 'Kim'.
2. Plants of the new *Phlox* had glossier and broader leaves than plants of 'Kim'.
3. Inflorescences of plants of the new *Phlox* were rounded or dome-shaped whereas inflorescences of plants of 'Kim' were open and ragged in appearance.
4. Plants of the new *Phlox* and 'Kim' differed in flower color as plants of 'Kim' had light lilac-colored flowers.

BRIEF DESCRIPTION OF THE PHOTOGRAPHS

The accompanying colored photographs illustrate the overall appearance of the new *Phlox* plant showing the colors as true as it is reasonably possible to obtain in colored reproductions of this type. Colors in the photographs may differ slightly from the color values cited in the detailed botanical description which accurately describe the colors of the new *Phlox* plant.

The photograph on the first sheet comprises a side perspective view of typical flowering plants of 'Aurora'.

The photograph at the top of the sheet is a close-up view of a typical flowering plant of 'Aurora'.

DETAILED BOTANICAL DESCRIPTION

The aforementioned photographs and following observations, measurements and values describe plants grown during the spring and summer in one-gallon containers in a polyethylene-covered greenhouse and an outdoor nursery in Upper Tyrone Township, Pa. and under cultural practices typical of *Phlox* production. During the production of the plants, day temperature averaged 26° C. and night temperatures averaged 15° C. Plants were two years old when the photographs and description were taken. In the following description, color references are made to The Royal Horticultural Society Colour Chart, 1995 Edition, except where general terms of ordinary dictionary significance are used.

Botanical classification: *Phlox×hybrida* 'Aurora'.

Parentage:

*Female, or seed, parent*.—Unnamed seedling selection of *Phlox maculata*, not patented.

*Male, or pollen, parent*.—Unknown selection of *Phlox×hybrida*, not patented.

Propagation:

*Type*.—By stem cuttings.

*Time to initiate roots, summer*.—About three weeks at night temperatures about 15° C. and day temperatures about 26° C.

*Time to produce a rooted plant, summer*.—About six weeks at night temperatures about 15° C. and day temperatures about 26° C.

*Root description*.—Medium in thickness, fibrous; white in color.

*Rooting habit*.—Freely branching; medium density.

Plant description:

*Plant and growth habit*.—Herbaceous perennial; upright and mounding plant habit, columnar; vigorous growth habit; freely basal branching habit with about six to ten primary laterals developing per plant; relatively short internodes.

*Plant height*.—About 50 cm.

*Plant width (spread)*.—About 45 cm.

*Lateral branches*.—Length: About 50 cm. Diameter: About 2 mm. Internode length: About 2.5 cm to 3.5 cm; distally, close to 6 cm. Strength: Strong. Texture: Slightly pubescent. Color: Close to 144B, mottled and streaked with close to 184D.

Leaf description:

*Arrangement*.—Opposite, simple; sessile.

*Length*.—About 5 cm to 8 cm.

*Width*.—About 8 mm to 12 mm.

*Shape*.—Lanceolate.

*Apex*.—Acute.

*Base*.—Gradually tapering.

*Margin*.—Entire.

*Texture, upper and lower surfaces*.—Glabrous; thick; waxy.

*Venation pattern*.—Pinnate.

*Color*.—Developing and fully expanded leaves, upper surface: Close to 139B; venation, close to 139B. Developing and fully expanded leaves, lower surface: Close to 139C; venation, close to 139C.

Flower description:

*Flower form and flowering habit*.—Single rotate and salverform flowers arranged in terminal compound panicles; panicles rounded and dome-shaped; freely flowering habit with about 80 to 100 flowers developing per inflorescence; flowers face mostly upright to outwardly.

*Fragrance*.—Moderately fragrant; sweet.

*Natural flowering season*.—Early flowering habit, plants begin flowering about six weeks after planting; plants flowering continuously from mid-spring to early summer in Pennsylvania.

*Postproduction longevity*.—Flowers last about five days on the plant and as a cut flower; flowers not persistent.

*Flower buds*.—Height: About 2.5 cm. Diameter: About 3.5 mm. Shape: Elongated oblong. Color: Close to 74C.

*Inflorescence height*.—About 6 cm to 16 cm.

*Inflorescence diameter*.—About 4 cm to 14 cm.

*Flower diameter*.—About 2.5 cm.

*Flower depth*.—About 2 cm.

*Flower throat diameter*.—About 1.8 mm.

*Flower tube length*.—About 2 cm.

*Flower tube diameter, at base*.—About 1.5 mm.

*Petals*.—Quantity per flower and arrangement: Typically five in a single whorl; petals fused at the base into a narrow tube. Lobe length: About 1.1 cm. Lobe width: About 9 mm. Shape: Rhomboidal. Apex: Obtuse. Margin: Entire, undulate. Texture: Petal lobes, upper and lower surfaces: Smooth, glabrous. Throat: Smooth, glabrous. Tube: Smooth, glabrous. Color: Developing petal lobes, upper surface: Close to 155D; towards the base, shaded with close to 74B. Developing petal lobes, lower surface: Close to 155D shaded with close to 74B. Fully expanded petal lobes, upper surface: Close to 155D shaded with close to 74B. Fully expanded petal lobes, lower surface: Close to 155D shaded with close to 74D. Flower throat: Close to 74D. Flower tube: Close to 74D

*Sepals*.—Quantity per flower and arrangement: Typically five in a single whorl, fused towards the base into a slender tube. Length: About 7 mm. Width: About 1.5 mm. Shape: Lanceolate. Apex: Acute. Margin: Entire, membraneous. Texture, upper and lower surfaces: Smooth, glabrous. Color, upper and lower surfaces: Close to 141B.

*Peduncles*.—Length: About 1.5 cm to 2 cm. Diameter: About 0.8 mm. Angle: Erect. Strength: Strong. Texture: Pilose. Color: Close to 144B.

*Pedicels*.—Length: About 3 mm to 4 mm. Diameter: About 0.7 mm. Angle: About 30° from peduncle axis. Strength: Strong. Texture: Pilose. Color: Close to 144B.

*Reproductive organs*.—Stamens: Quantity per flower: Typically five. Filament length: About 1 mm. Anther shape: Oval. Anther length: About 2 mm. Anther color: Close to 17A. Pollen amount: Scarce. Pollen color: Close to 17A. Pistils: Quantity per flower: One. Pistil length: About 2 cm. Stigma shape: Triparted. Stigma color: Close to 154C. Style length: About 1.7 cm. Style color: Close to 154C. Ovary color: Close to 141B.

*Seeds and fruits*.—Seed and fruit development have not been observed on plants of the new *Phlox* plant.

Disease & pest resistance: Plants of the new *Phlox* have been observed to be resistant to Powdery Mildew. Plants of the new *Phlox* have not been observed to be resistant to pests and other pathogens common to *Phlox* plants.

Garden performance: Plants of the new *Phlox* have been observed to have good garden performance and tolerate rain and wind and to temperatures ranging from about −30° C. to 45° C.

It is claimed:

1. A new and distinct *Phlox* plant named 'Aurora' as illustrated and described.

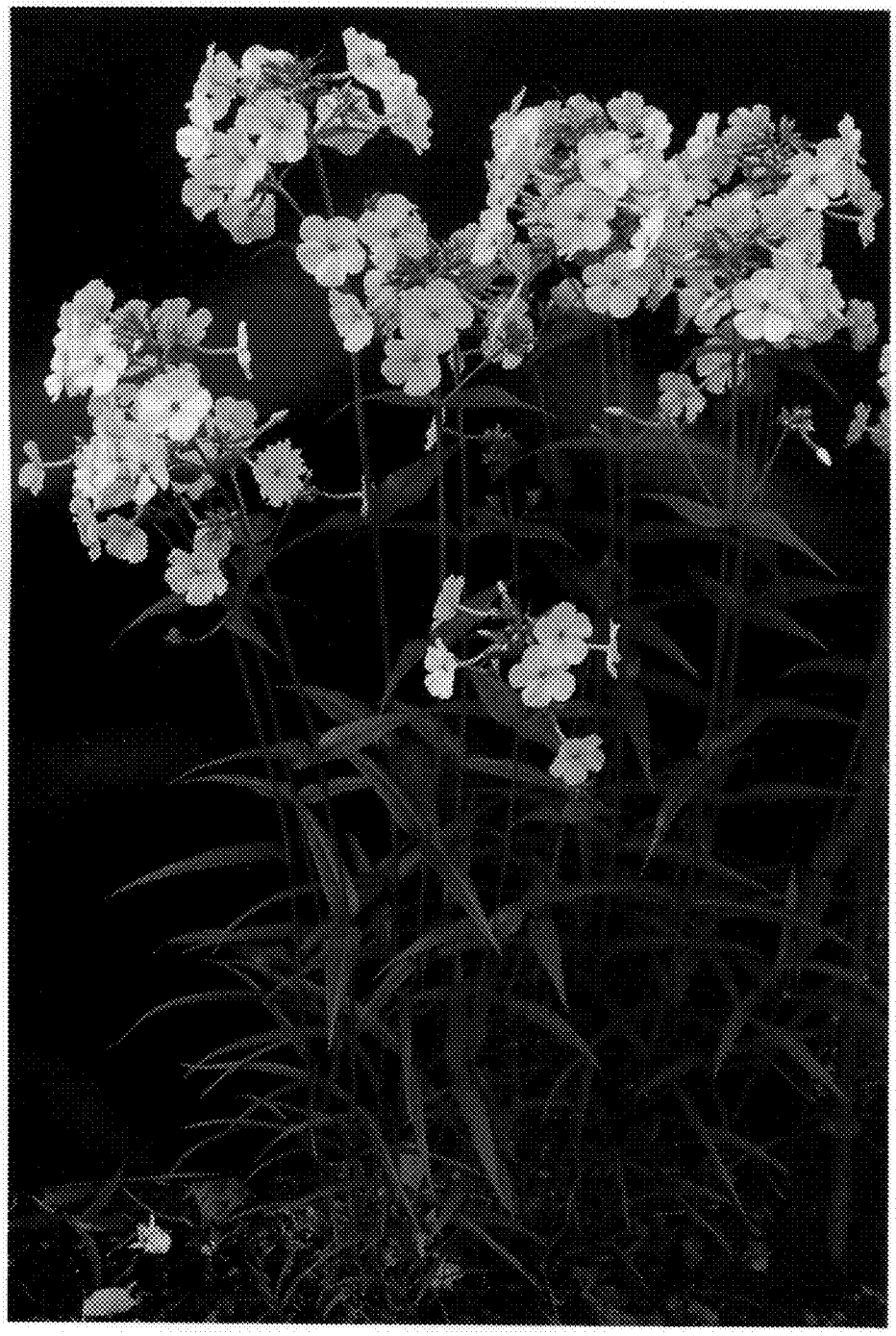

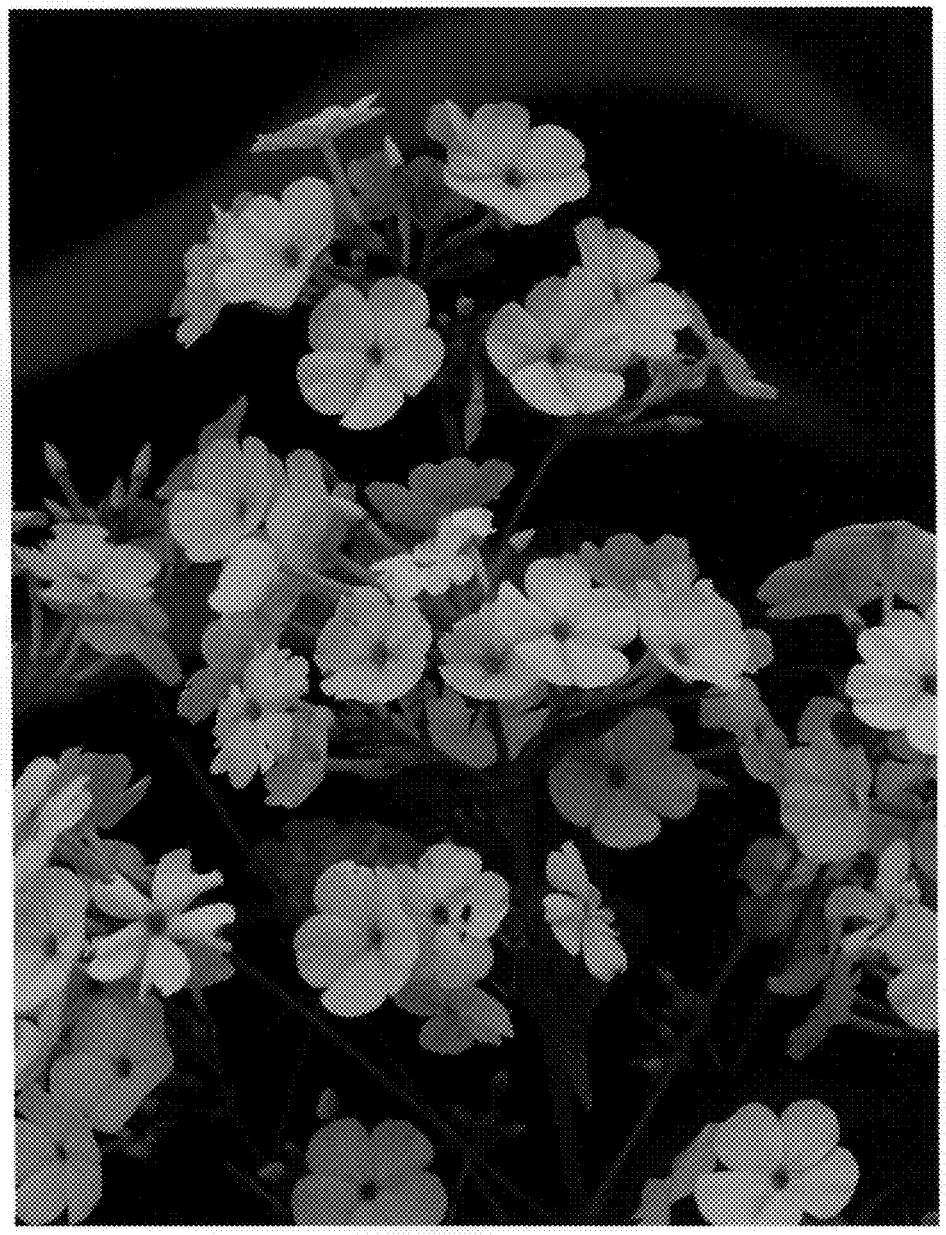

* * * * *